(12) United States Patent
Steed et al.

(10) Patent No.: US 10,881,826 B2
(45) Date of Patent: Jan. 5, 2021

(54) METHOD OF OBTAINING A 3D SCAN OF A PATIENTS FACE

(71) Applicant: KONINKLIJKE PHILIPS N.V., Eindhoven (NL)

(72) Inventors: Daniel Steed, North Huntingdon, PA (US); Robert William Baiko, Pittsburgh, PA (US); Richard Andrew Sofranko, Finleyville, PA (US)

(73) Assignee: Koninklijke Philips N.V., Eindhoven (CH)

(*) Notice: Subject to any disclaimer, the term of this patent is extended or adjusted under 35 U.S.C. 154(b) by 95 days.

(21) Appl. No.: 16/222,165

(22) Filed: Dec. 17, 2018

(65) Prior Publication Data

US 2019/0217035 A1 Jul. 18, 2019

Related U.S. Application Data

(60) Provisional application No. 62/608,178, filed on Dec. 20, 2017.

(51) Int. Cl.
| | | |
|---|---|---|
| *A61M 16/06* | (2006.01) | |
| *G06Q 10/08* | (2012.01) | |
| *G06K 9/00* | (2006.01) | |
| *G16H 20/00* | (2018.01) | |

(52) U.S. Cl.
CPC ........ *A61M 16/0605* (2014.02); *A61M 16/06* (2013.01); *G06K 9/00221* (2013.01); *G06Q 10/083* (2013.01); *G16H 20/00* (2018.01); *A61M 2016/0661* (2013.01); *A61M 2205/3553* (2013.01); *A61M 2205/3584* (2013.01);

(Continued)

(58) Field of Classification Search
CPC .............. A61M 16/06; A61M 16/0605; A61M 16/0661; G06Q 10/083
See application file for complete search history.

(56) References Cited

U.S. PATENT DOCUMENTS

| | | | |
|---|---|---|---|
| 2001/0026272 A1 | 10/2001 | Feld | |
| 2006/0235877 A1* | 10/2006 | Richard | ................. G06Q 50/22 |
| 2008/0060652 A1 | 3/2008 | Selvarajan | |

(Continued)

FOREIGN PATENT DOCUMENTS

| | | |
|---|---|---|
| WO | WO2005118041 A1 | 12/2005 |
| WO | WO2011073813 A1 | 6/2011 |

(Continued)

OTHER PUBLICATIONS

Grunewald, Scott J. "Metannason Turns to 3D Scanning and 3D Printing to Customize the Respere CPAP Mask". 3D Printing Industry, acquired from https://3dprintingindustry.com/news/metamason-turns-3d-scanning-3d-printing-customize-respere-cpap-mask-30380/, Jul. 25, 2014. (Year: 2014).*

(Continued)

*Primary Examiner* — Michael A Lyons
(74) *Attorney, Agent, or Firm* — Michael W. Haas

(57) ABSTRACT

A method of obtaining a 3D scan of a patient's face includes receiving a request for a 3D scanner from the patient, sending the 3D scanner to the patient, receiving the 3D scan of the patient's face obtained from the 3D scanner from the patient, receiving the 3D scanner from the patient, and using the 3D scan of the patient's face to make, select, or customize a patient interface device for the patient.

17 Claims, 4 Drawing Sheets

(52) U.S. Cl.
CPC ... *A61M 2205/502* (2013.01); *A61M 2205/52* (2013.01); *A61M 2207/00* (2013.01)

(56) References Cited

U.S. PATENT DOCUMENTS

| | | |
|---|---|---|
| 2008/0078396 A1 | 4/2008 | Janbakhsh |
| 2012/0245962 A1 | 9/2012 | Smith |
| 2012/0305003 A1 | 12/2012 | Mark |
| 2015/0157822 A1* | 6/2015 | Karpas ............... G06F 30/00 128/206.24 |
| 2015/0195434 A1 | 7/2015 | Kwon |
| 2015/0250971 A1 | 9/2015 | Bachelder |
| 2016/0092645 A1 | 3/2016 | Vlutters |
| 2016/0354571 A1 | 12/2016 | Grashow |
| 2017/0080172 A1 | 3/2017 | Karpas |
| 2017/0128686 A1 | 5/2017 | Margaria |
| 2017/0132565 A1 | 5/2017 | Beadles |
| 2017/0274166 A1* | 9/2017 | Tang Ee Ho ........ A61B 5/1075 |
| 2018/0267518 A1* | 9/2018 | Hassman ........... G05B 19/4183 |
| 2019/0160247 A1* | 5/2019 | Kimmel ................ G16H 20/40 |

FOREIGN PATENT DOCUMENTS

| | | |
|---|---|---|
| WO | WO2015195303 A1 | 12/2015 |
| WO | WO2016000040 A1 | 1/2016 |
| WO | WO2017102899 A1 | 6/2017 |

OTHER PUBLICATIONS

CSIRO. "3D printing to treat sleep apnoea". YouTube video acquired from https://www.youtube.com/watch?v=QiV5LXIbEFA, May 6, 2014. (Year: 2014).*

* cited by examiner

METHOD OF OBTAINING A 3D SCAN OF A PATIENTS FACE

CROSS-REFERENCE TO RELATED APPLICATIONS

This patent application claims the priority benefit under 35 U.S.C. § 119(e) of U.S. Provisional Application No. 62/608,178, filed on Dec. 20, 2017, the contents of which are herein incorporated by reference.

BACKGROUND OF THE INVENTION

1. Field of the Invention

The present invention pertains to a respiratory therapy, and, in particular, to a method of obtaining a 3D scan of a patient's face for use in selecting, customizing, or creating a patient interface device.

2. Description of the Related Art

Obstructive sleep apnea (OSA) is a condition that affects millions of people from around the world. OSA is characterized by disturbances or cessation in breathing during sleep. OSA episodes result from partial or complete blockage of airflow during sleep that lasts at least 10 seconds and often as long as 1 to 2 minutes. In a given night, people with moderate to severe apnea may experience complete or partial breathing disruptions as high as 200-500 per night. Because their sleep is constantly disrupted, they are deprived of the restorative sleep necessary for efficient functioning of body and mind. This sleep disorder has also been linked with hypertension, depression, stroke, cardiac arrhythmias, myocardial infarction and other cardiovascular disorders. OSA also causes excessive tiredness.

Non-invasive ventilation and pressure support therapies involve the placement of a patient interface device, which is typically a nasal or nasal/oral mask, on the face of a patient to interface the ventilator or pressure support system with the airway of the patient so that a flow of breathing gas can be delivered from the pressure/flow generating device to the airway of the patient.

Typically, patient interface devices include a mask shell or frame having a cushion attached to the shell that contacts the surface of the patient. The mask shell and cushion are held in place by a headgear that wraps around the head of the patient. The mask and headgear form the patient interface assembly. A typical headgear includes flexible, adjustable straps that extend from the mask to attach the mask to the patient.

Because patient interface devices are typically worn for an extended period of time, a variety of concerns must be taken into consideration. For example, in providing CPAP to treat OSA, the patient normally wears the patient interface device all night long while he or she sleeps. One concern in such a situation is that the patient interface device is as comfortable as possible, otherwise the patient may avoid wearing the interface device, defeating the purpose of the prescribed pressure support therapy. Additionally, an improperly fitted mask can cause red marks or pressure sores on the face of the patient. Another concern is that an improperly fitted patient interface device can include gaps between the patient interface device and the patient that cause unwanted leakage and compromise the seal between the patient interface device and the patient. A properly fitted patient interface device should form a robust seal with the patient that does not break when the patient changes positions or when the patient interface device is subjected to external forces. Thus, it is desirable to properly fit the patient interface device to the patient.

3D scanning can be employed in order to improve the fit of the patient interface device to the patient. Generally, a 3D scan can be taken of the patient's face and then the information about the patient's face can be used to select the best fitting patient interface device, to customize an existing patient interface device, or to custom make a patient interface device that fits the patient well.

A 3D scan is a critical element to generating the custom geometry for customizing or custom making a patient interface device for a patient. The 3D scan is also very useful for selecting a properly fitting patient interface device. In order to accurately gather the geometry of a patient's face, a 3D scanner typically comprises a fixture including more than one camera. 3D scanners can be expensive devices with some hand held 3D scanners reaching 20K USD. It is not practical for the patient to purchase a 3D scanner in order to obtain the 3D scan of the patient's face. The patient will typically travel to a medical provider's facility or another facility where a 3D scanner is located in order to use the 3D scanner and obtain a 3D scan of their face. The travel to the medical provider's facility to use the 3D scanner is an inconvenience for the user. Additionally, not all medical provider facilities will have a 3D scanner. The patient may have to travel a long distance to reach a medical provider facility with a 3D scanner.

SUMMARY OF THE INVENTION

In accordance with aspects of the disclosed concept, a method of obtaining a 3D scan of a patient's face comprises: receiving a request for a 3D scanner from the patient; sending the 3D scanner to the patient; receiving the 3D scan of the patient's face obtained from the 3D scanner from the patient; receiving the 3D scanner from the patient; and using the 3D scan of the patient's face to make, select, or customize a patient interface device for the patient.

In accordance with other aspects of the disclosed concept, a method of obtaining a 3D scan of a patient's face comprises: sending a request for a 3D scanner from the patient to a provider of patient interface devices; receiving the 3D scanner from the provider; using, by the patient, the 3D scanner to obtain the 3D scan of the patient's face; and sending the 3D scan to the provider.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the term "3D scanner" shall mean a device being capable of creating a 3D scan of an object such as a patient's face. In some example embodiments, the 3D scanner may be a device having multiple cameras and being capable of creating a 3D scan of an object. Also, in some example embodiments, the 3D scanner may comprise a single camera along with a structured light projector. The structured light projector may provide a grid or pattern whose projected image can be gathered by the camera and decoded to provide absolute dimensional distances of the captured object to create a 3D scan of the object.

Figure 1:
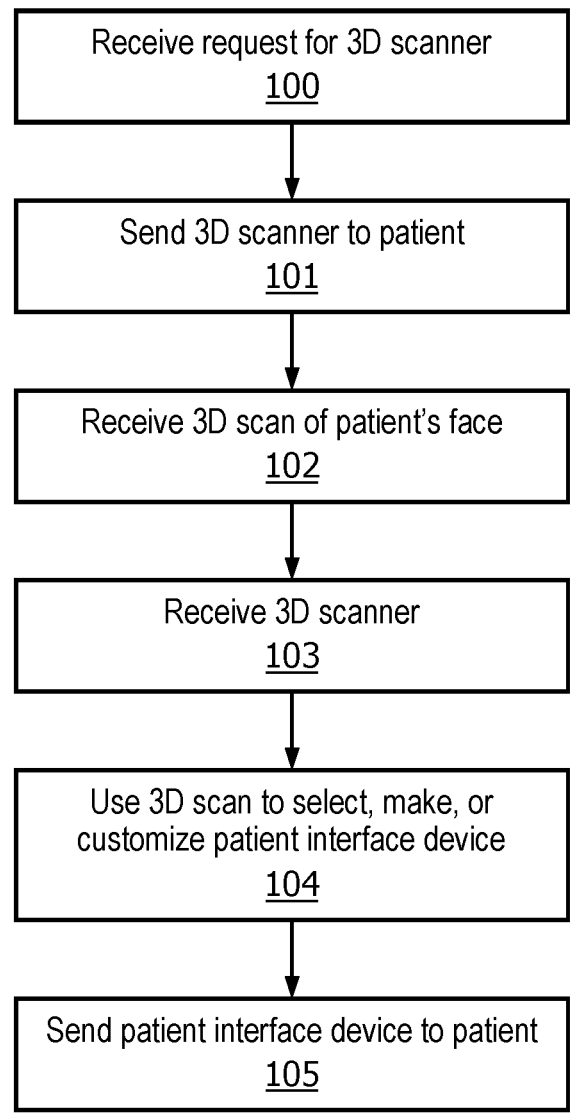
FIG. 1 is a flowchart of a method of obtaining a 3D scan of a patient's face according to an exemplary embodiment of the disclosed concept from the perspective of a provider.
Figure 2:
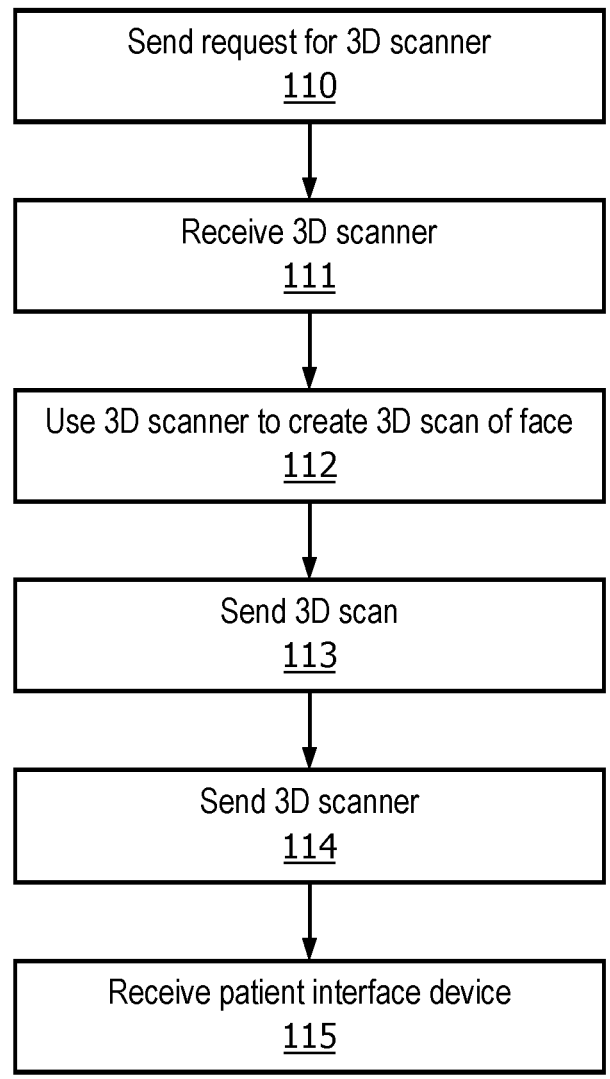
FIG. 2 is a flowchart of a method of obtaining a 3D scan of a patient's face according to an exemplary embodiment of the disclosed concept from the perspective of a patient.

FIG. 1 is a flowchart of a method of obtaining a 3D scan of a patient's face in accordance with an exemplary embodiment of the disclosed concept. The flowchart of FIG. 1 is shown from the perspective of a provider of patient interface devices. FIG. 2 is another flowchart of a method of obtaining a 3D scan of a patient's face in accordance with an exemplary embodiment of the disclosed concept. FIGS. 3-6 are conceptual diagrams illustrating the methods shown in the flowcharts of FIGS. 1 and 2 in accordance with an exemplary embodiment of the disclosed concept.

FIG. 3-6 illustrate a warehouse 2, a 3D scanner 4, a patient 6, the patient's residence 8, a medical provider facility 10, a manufacturing facility 12, and a patient interface device 14 which will be referenced in the description of FIGS. 1 and 2.

Figure 3:
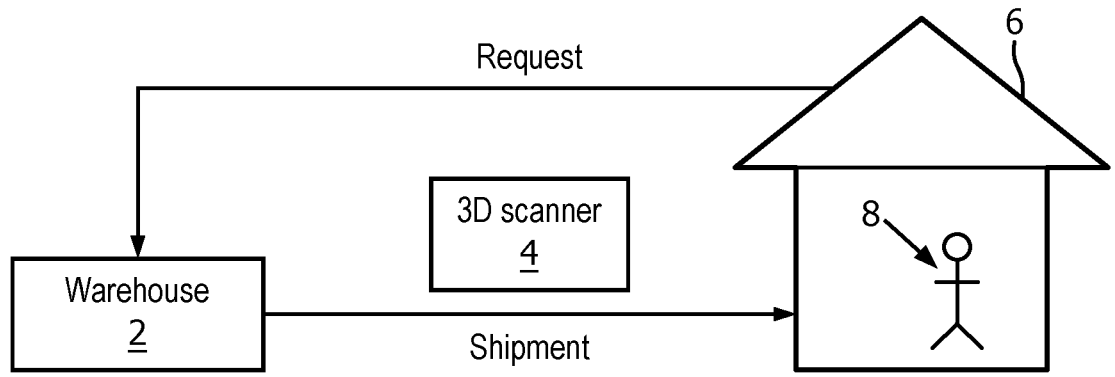
FIGS. 3-6 are conceptual diagrams illustrating a method of obtaining a 3D scan of a patient's face in accordance with an exemplary embodiment of the disclosed concept.
Figure 4:
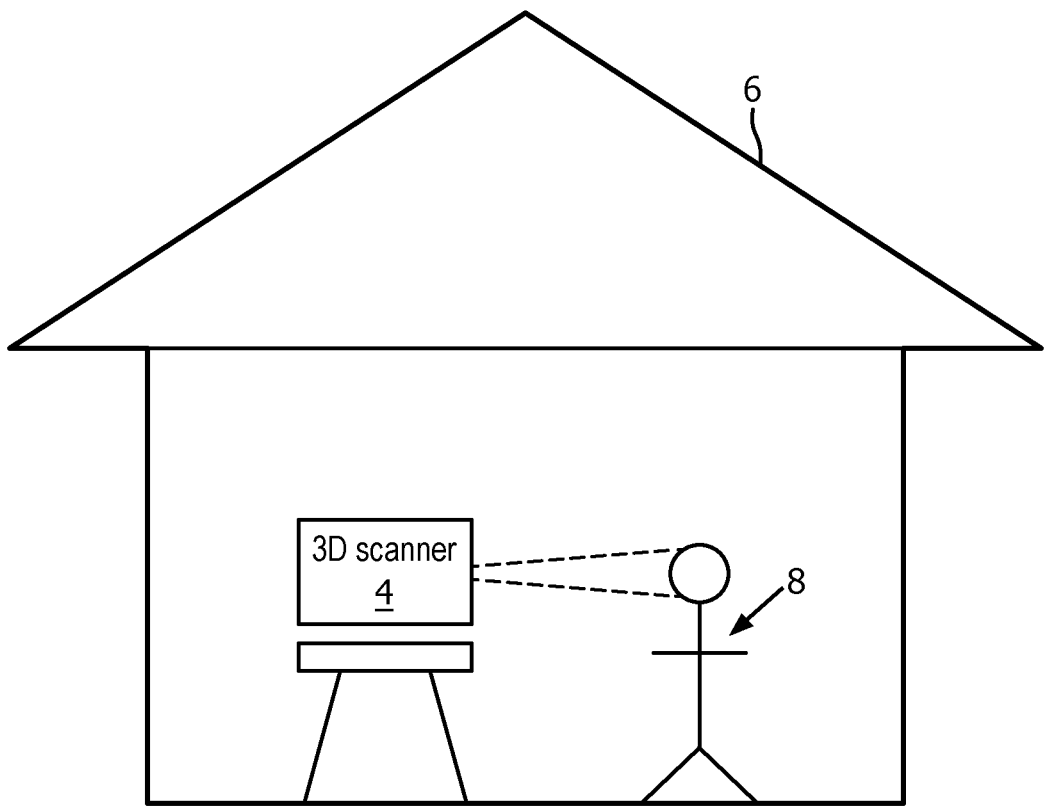

Referring to FIG. 1, the method of obtaining the 3D scan of patient's 6 from the perspective of a provider begins at 100 where the provider receives a request for a 3D scanner such as 3D scanner 4 shown in FIG. 3. The provider may be an entity that manufactures and/or provides patient interface device 14 (e.g., a mask used for providing respiratory therapy to patient 8) to patient 8. The provider may be, for example and without limitation, a healthcare company, or another type of company or entity, that manufactures and/or provides patient interface device 14 to patient 8. The provider may have several facilities such as, without limitation, warehouse 2, medical provider facility 10, and manufacturing facility 12.

The provider may receive the request from patient 8 in any suitable manner. For example and without limitation, the provider may receive the request for 3D scanner 4 electronically. In some example embodiments, patient 8 may send a request for 3D scanner 4 to the provider via an internet portal or other suitable electronic methods such as through an application in a mobile phone. However, it will be appreciated by those having ordinary skill in the art that the request may be received from patient 6 in any other suitable manner. FIG. 3 shows the request being received at warehouse 2, which may be a facility of the provider. However, it will be appreciated by those having ordinary skill in the art that the request may be received at other provider locations without departing from the scope of the disclosed concept.

3D scanner 4 may be any type of 3D scanner suitable for scanning a body part of patient 8, such as patient's 8 face. In some example embodiments of the disclosed concept, 3D scanner 4 may be a handheld 3D scanner. In some example embodiments, 3D scanner 4 uses at least two 2D images to create the 3D scan. For example, 3D scanner 4 may include multiple cameras that capture multiple 2D images of patient's 8 face. 3D scanner 4 then overlays and stitches together the 2D images. Each point on the (at least) 2D images is triangulated mathematically to reconstruct the scale and location in space to create the 3D scan. The more overlapping 2D images that are used, the greater the resolution and reliability of the resulting 3D scan.

In some example embodiments, 3D scanner 4 may include a single camera along with additional equipment that allows it to properly capture multiple images of patient's 8 face that can be used to create a 3D can of patient's 8 face. For example, 3D scanner 4 may include a camera along with mirrors arranged such that the camera can capture multiple images of patient's 8 face. As another example, 3D scanner 4 may include a single camera along with a mechanism to move the camera to a different location so that the camera can capture multiple images of patient's 8 face from different locations. As yet another example, 3D scanner 4 may include a single camera along with an interactive interface that instructs a user through indicators or other mechanisms how to move the camera to capture multiple images.

In some example embodiments, 3D scanner 4 may comprise a single camera along with a structured light projector. The structured light projector may project a grid or pattern on patient's 8 face that can be gathered by the camera and decoded to provide absolute dimensional distances of the captured object to create a 3D scan of patient's 8 face.

After receiving the request for 3D scanner 4, the method proceeds to 101 where the provider sends 3D scanner 4 to patient 8. In the example embodiment shown in FIG. 3, 3D scanner 4 is shipped from the provider's warehouse 2 to patient's residence 6 where it can be received by patient 8. However, the disclosed concept is not limited to shipping 3D scanner 4 from warehouse 2 to patient's residence 6. It will be appreciated by those having ordinary skill in the art that 3D scanner 4 may be shipped from a different location and be received at a different location. For example, 3D scanner 4 may be shipped to any address of patient's choosing 8 without departing from the scope of the disclosed concept. In some example embodiments, additional information, such as instructions for operating 3D scanner 4 may be sent to patient 8 as well.

After sending 3D scanner 4 to patient 8, the method proceeds to 102 where the provider receives a 3D scan of patient's 8 face. Patient 8 may use the 3D scanner 4 to obtain the 3D scan of their face and send the 3D scan to the provider, which will be described in more detail with respect to FIG. 2. The provider may receive the 3D scan of patient's 8 face electronically or in any other suitable manner. For example, the provider may receive the 3D scan of patient's 8 face from internal memory in the 3D scanner 4, via a network communication, or via a removable memory. In some example embodiments, the 3D scan is retained in the memory of 3D scanner 4 and the provider receives the 3D scan in conjunction with the return of 3D scanner 4. The 3D scan may be considered sensitive data. In some example embodiments, the provider may download the 3D scan off of the internal memory and then erase the 3D scan from the internal memory of 3D scanner 4. 3D scanner may then be sent to another patient without allowing one patient to access the 3D scan of another patient.

In some example embodiments, 3D scanner 4 includes a communication interface that may communicate via one or more networks such as the internet or a cellular communication network. Patient 8 may use 3D scanner 4 to upload the 3D scan of patient's 8 face to the provider via the communication interface of 3D scanner 4. In yet other example embodiments, 3D scanner 4 may include a removable memory (e.g., without limitation, a USB drive, a smart card, or other suitable removable memories). The 3D scan of patient's 8 face may be stored on the removable memory. Patient 8 may remove the removable memory and send it to the provider. The provider may receive the 3D scan of patient's 8 face at a medical provider facility 10 or any other suitable location. In some example embodiments, 3D scanner 4 and the 3D scan of patient's 8 face are returned together to a location such as warehouse 2. It will be appreciated that 3D scanner 4 and the 3D scan of patient's 8 face may be received by the provider at the same or different locations.

Figure 5:
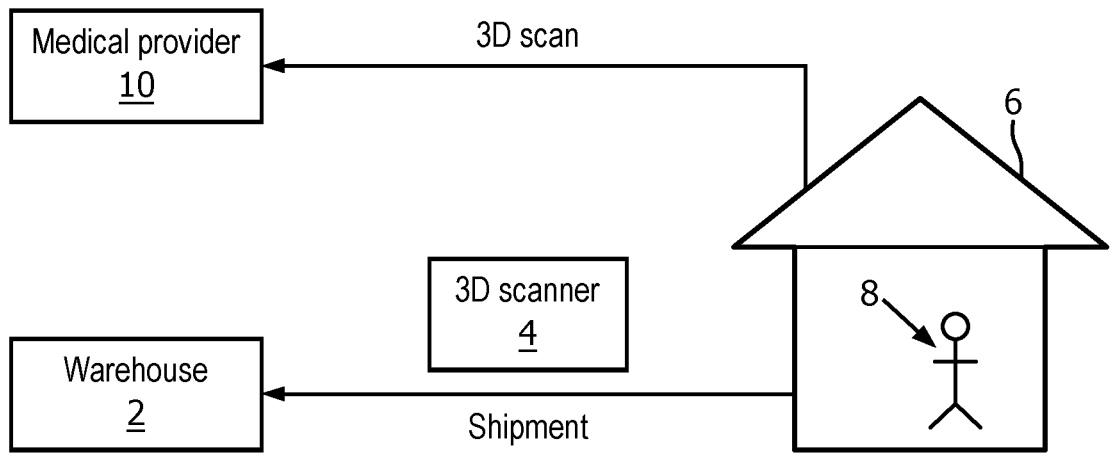

At 103, the provider receives 3D scanner 4 from patient 8. Patient 8 may ship 3D scanner 4 back to the same location it was shipped from, such as warehouse 2, as is shown in FIG. 5, or to another location designated by the provider.

At 104, the provider uses the 3D scan of patient's 8 face to select, make, or customize patient interface device 14 for patient 8. For example, the provider may use the 3D scan of patient's 8 face to analyze the geometry of patient's 8 face to determine an optimally fitting patient interface device. Based on the analysis, the provider may select an existing patient interface device having an optimal fit from among the selections, customize an existing patient interface device (e.g., adjusting components or custom manufacturing selected components) to have an optimal fit, or create a patient interface device with an optimal fit. The provider may select, customize, and/or create patient interface device 14 at manufacturing facility 12, as is shown in FIG. 6, or at any other suitable facility.

Figure 6:
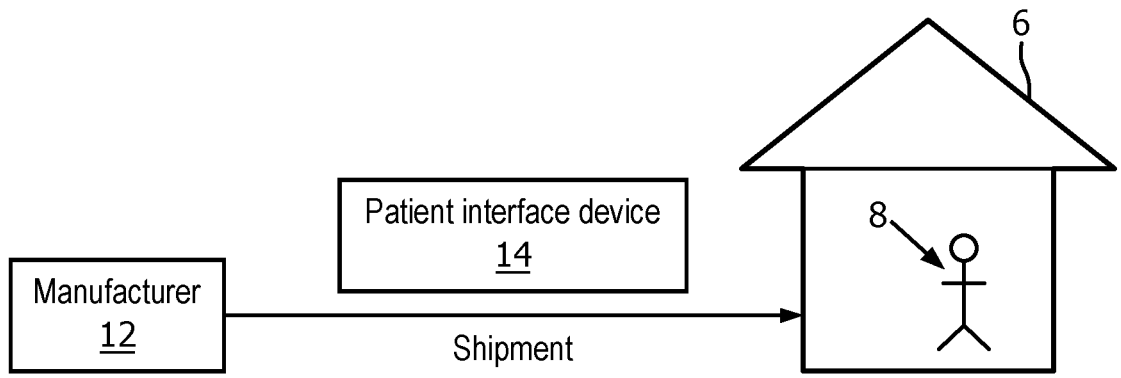

After patient interface device 14 has been selected, customized, or created, the provider sends patient interface device 14 to patient 8, as is shown for example in FIG. 6. It will be appreciated by those having ordinary skill in the art that patient interface device 14 may be sent to patient's residence 6 or any other suitable location such as an address designated by patient 8.

The method may be repeated for a second patient and so on. For example, after the provider receives 3D scanner 4, the provider may receive a request for 3D scanner 4 from a second patient. The provider may then send the same 3D scanner 4 that was received from patient 8 to the second patient. The method may continue repeating as needed so that the same 3D scanner 4 can be sent and received from numerous patients in order to obtain 3D scans of the patient's faces without the need for the patients to individually purchase 3D scanners or travel to medical provider facilities to use a 3D scanner.

Referring to FIG. 2, the method of obtaining the 3D scan of patient's 8 face according to an exemplary embodiment from the perspective of patient 8 is shown. The method begins at 110 with patient 8 sending a request to the provider for a 3D scanner such as 3D scanner 4. As previously described, the request may be sent to the provider in any suitable manner. In some example embodiments, patient 8 may determine that the request for 3D scanner 4 is needed based on a diagnosis. For example, patient 8 may visit a medical provider such as a sleep study lab to determine that respiratory therapy is recommended and that 3D scanner 4 should be requested to assist with obtaining a patient interface device. In some example embodiments, the diagnosis may be received from patient's residence 6 from a remote diagnosis obtained through a web browser, a mobile phone application, or any other suitable manner for obtaining a remote diagnosis. By receiving a remote diagnosis, patient 8 may complete the entire process of obtaining patient interface device 14 without leaving patient's residence 6.

After sending the request for 3D scanner 4 to the provider, the method proceeds to 111 where patient 8 receives 3D scanner 4. As previously described, 3D scanner 4 is sent from the provider to patient's residence 6 or any other suitable location. Once patient 8 has received 3D scanner 4, the method proceeds to 112.

At 112, patient 8 uses 3D scanner 4 to obtain the 3D scan of their face. The 3D scan may be obtained in patient's residence 6, for example. In some example embodiments of the disclosed concept, patient 8 may receive additional information, such as instructions for operating 3D scanner 4 from the provider. Patient 8 may then follow the received instructions to operate 3D scanner 4 and obtain the 3D scan of their face. Also, in some example embodiments, 3D scanner 4 may have an interface (e.g., a touch screen display or other combination of a display and input device) that provides interactive instructions to guide patient 8 through the process of operating 3D scanner 4 to obtain the 3D scan of their face. In yet another example embodiment, patient 8 may use an interactive tool such as an application for a mobile phone, a website, or another type of tool to receive interactive instructions to guide patient 8 through the process of operating 3D scanner 4 to obtain the 3D scan of their face. 3D scanner 4 may be an unfamiliar device to patient 8 so instructions or interactive tools will be beneficial in allowing patient 8 to properly operate 3D scanner 4 and properly obtain the 3D scan of their face. While the above example embodiments allow patient 8 to operate 3D scanner 4 on their own, it will be appreciated that in some example embodiments, a healthcare provider or technician may travel to patient's residence 6 and operate 3D scanner 4 for patient 8 to obtain the 3D scan of their face.

After obtaining the 3D scan of patient's 8 face, the method proceeds to 113, where patient 8 sends the 3D scan to the provider. As previously described, the 3D scan may be sent to the provider via memory included in the 3D scanner 4, via a network communication, or via a removable memory. At 114, patient 8 sends 3D scanner 4 to the provider. 3D scanner 4 may be sent back to warehouse 2 or any other suitable location designated by the provider. At 115, patient 8 receives patient interface device 14 from the provider. Patient interface device 14 may be selected, customized, or created based on the 3D scan of patient's 8 face.

In accordance with the example embodiment of FIG. 2, patient 8 is able to receive 3D scanner 4 from the provider and return it and the 3D scan to the provider. Patient 8 does not need to purchase a 3D scanner or travel to a medical provider facility to use a 3D scanner to obtain the 3D scan of their face. The methods in the example embodiments of FIGS. 1 and 2 provide a convenient and economical method of obtaining the 3D scan of patient's 8 face for both the provider and patient 8.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of obtaining a 3D scan of a patient's face, the method comprising:
   receiving a request for a 3D scanner from the patient;
   sending the 3D scanner to the patient;
   receiving the 3D scan of the patient's face obtained from the 3D scanner from the patient;
   receiving the 3D scanner from the patient; and
   using the 3D scan of the patient's face to make, select, or customize a patient interface device for the patient.

2. The method of claim 1, wherein sending the 3D scanner includes sending the 3D scanner to the patient's residence.

3. The method of claim 1, wherein sending the 3D scanner includes sending instructions for operating the 3D scanner along with the 3D scanner.

4. The method of claim 1, wherein the 3D scanner includes an internal memory, and wherein receiving the 3D scan includes receiving the 3D scan from memory included in the 3D scanner.

5. The method of claim 4, further comprising:
   erasing the 3D scan from the memory of the 3D scanner after receiving the 3D scan.

6. The method of claim 1, wherein the 3D scanner includes a removable memory, and wherein receiving the 3D scan includes receiving the 3D scan from the removable memory.

7. The method of claim 1, wherein the 3D scanner includes a communication interface structured to transmit the 3D scan via a network, and wherein receiving the 3D scan includes receiving the 3D scan via the network.

8. The method of claim 1, wherein using the 3D scan of the patient's face to make, select, or customize a patient interface device for the patient includes analyzing the 3D scan of the patient's face to make a patient interface device with an optimal fit, selecting a patient interface with an optimal fit, or customizing a patient interface device to have an optimal fit.

9. The method of claim 1, further comprising sending the patient interface device to the patient.

10. The method of claim 1, further comprising:
    after receiving the 3D scanner, receiving a second request for a 3D scanner from a second patient; and
    sending the 3D scanner to the second patient.

11. A method of obtaining a 3D scan of a patient's face, the method comprising:
    sending a request for a 3D scanner from the patient to a provider of patient interface devices;
    receiving the 3D scanner from the provider;
    using, by the patient, the 3D scanner to obtain the 3D scan of the patient's face; and
    sending the 3D scan to the provider.

12. The method of claim 11, wherein receiving the 3D scanner includes receiving instructions for operating the 3D scanner with the 3D scanner, and wherein using the 3D scanner includes following the instructions to operate the 3D scanner.

13. The method of claim 11, wherein the 3D scanner includes an interface including interactive instructions for operating the 3D scanner, wherein using the 3D scanner includes following the interactive instructions to operate the 3D scanner.

14. The method of claim 11, wherein using the 3D scanner includes following instructions provided by an interactive tool separate from the 3D scanner, and wherein the interactive tool is included in an application for a mobile phone or a website.

15. The method of claim 11, wherein the 3D scanner includes a removable memory, and wherein sending the 3D scan includes sending the removable memory to the provider.

16. The method of claim 11, wherein the 3D scanner includes a communication interface structured to transmit the 3D scan via a network, and wherein sending the 3D scan includes sending the 3D scan to the provider via the network.

17. The method of claim 11, further comprising:
    receiving a patient interface device from the provider, wherein the patient interface device is made, selected, or customized by the provider using the 3D scan.

* * * * *